(12) United States Patent　(10) Patent No.: US 8,593,286 B2
Razoumov et al.　(45) Date of Patent: Nov. 26, 2013

(54) SYSTEM AND METHOD FOR WIRELESS MONITORING OF SPORTS ACTIVITIES

(75) Inventors: Leonid Razoumov, Riverdale, NY (US); Donald J. Bowen, Madison, NJ (US); Robert R. Miller, II, Convent Stn., NJ (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 414 days.

(21) Appl. No.: 12/957,558

(22) Filed: Dec. 1, 2010

(65) Prior Publication Data

US 2012/0139731 A1　Jun. 7, 2012

(51) Int. Cl.
*G08B 23/00*　(2006.01)

(52) U.S. Cl.
USPC .................................. 340/573.1; 340/539.11

(58) Field of Classification Search
USPC .................. 340/539.1, 539.11, 539.24, 573.1
See application file for complete search history.

(56) References Cited

U.S. PATENT DOCUMENTS

| | | | | |
|---|---|---|---|---|
| 7,602,301 B1 * | 10/2009 | Stirling et al. | ............. | 340/573.1 |
| 7,741,975 B2 * | 6/2010 | Shum et al. | ................... | 340/692 |
| 7,821,407 B2 * | 10/2010 | Shears et al. | ............... | 340/573.1 |
| 7,825,815 B2 * | 11/2010 | Shears et al. | ............... | 340/573.1 |
| 7,978,081 B2 * | 7/2011 | Shears et al. | ............... | 340/573.1 |
| 8,013,754 B2 * | 9/2011 | Shum et al. | ................... | 340/692 |
| 8,188,877 B2 * | 5/2012 | Shum et al. | ................... | 340/692 |
| 2010/0117837 A1 * | 5/2010 | Stirling et al. | ............. | 340/573.1 |
| 2010/0201512 A1 * | 8/2010 | Stirling et al. | ........... | 340/539.11 |
| 2012/0147009 A1 * | 6/2012 | Benzel et al. | ................. | 345/440 |
| 2012/0188083 A1 * | 7/2012 | Miller, II | ................... | 340/573.1 |

\* cited by examiner

*Primary Examiner* — Travis Hunnings
(74) *Attorney, Agent, or Firm* — Turocy & Watson, LLP

(57) ABSTRACT

The subject disclosure provides a system and method for wireless monitoring of sports activities. A subject participating in a sports activity is associated with biometric sensors which measure the subject's body movements. In one aspect, the system includes a sensor for continuously gathering biometric data from a subject performing a sports activity where the biometric data associated with the body movements of the subject. A wireless transceiver coupled to the sensor transmits the biometric data and a database engine receives the biometric data from the wireless transceiver and providing real-time feedback. The real-time feedback associated with the biometric data from the subject is characterized by instructions associated with the sports activity.

36 Claims, 10 Drawing Sheets

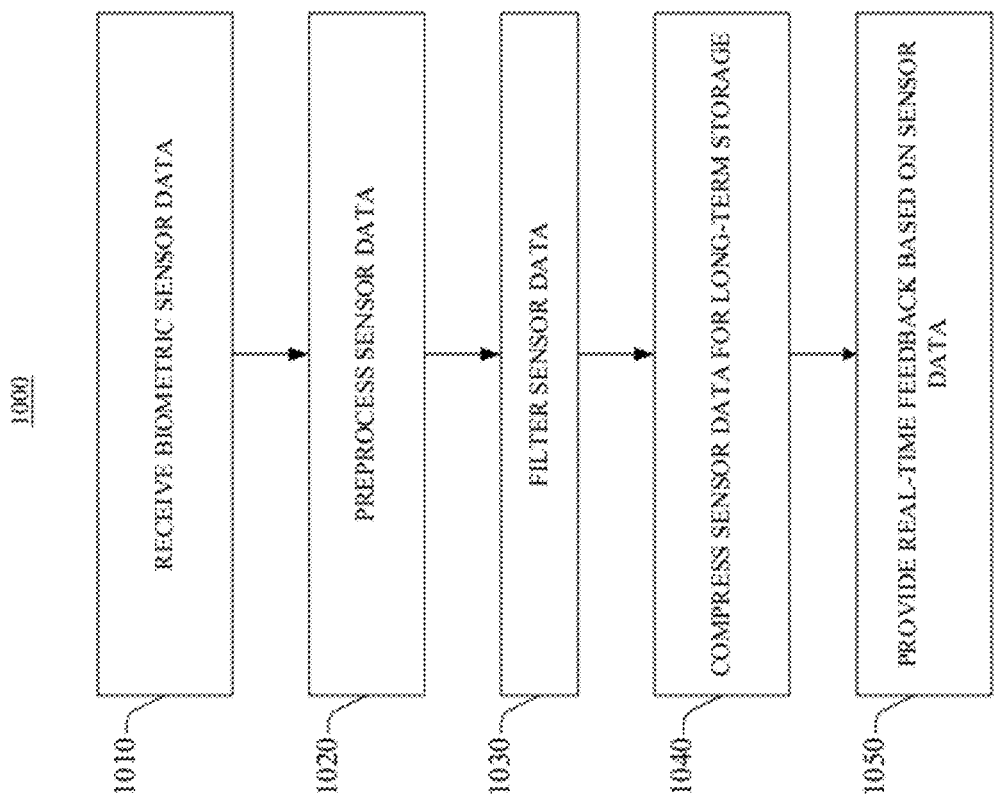

SYSTEM AND METHOD FOR WIRELESS MONITORING OF SPORTS ACTIVITIES

TECHNICAL FIELD

The subject disclosure relates generally to measurement and analysis of body movements, and more specifically, to communicating information related to such body movements over a network and providing feedback.

BACKGROUND

Conventional athletic training methods and techniques include weight lifting, jump training, sprint training, agility training, and the like. Each training regimen often requires extensive training supervision by a coach or trainer. As such, much of the efficiency and individualistic training focus is lost or even avoided. Limited personnel, unskilled personnel, and cost and time restraints make effective off-season training ineffective. Training regimens are generally segregated and conducted without looking at the effects to, or an integration with, other training regimens. Further, without the proper implementation and timing for the individual training tasks, athletes are unable to properly focus the workouts in a manner that serves to maximize the individual's needs against the goals of the specific regimen (i.e., timing, strength, jumping, etc.) or the aggregate regimen schedule.

Additionally, participants in sports, athletics, and recreational activities often desire to measure their progress relative to their earlier performance or to a performance benchmark such as a famous athlete. Coaches and trainers may desire to monitor the performance of a player or a team as a whole. Further, medical patients who have suffered an injury that restricts movement of a limb or joint may desire to track their improvement during rehabilitation, and an attending health care provider may desire an object measurement of the improvement.

Sensors can be attached to portions of the body to measure body movements. Data from the sensors can be analyzed to determine characteristics of the body movement (e.g., a range of motion). Today's sensors frequently store data only locally in the device. The data can be displayed on a local readout device that is part of the sensor. Most training environments require the trainee to "dump" readings from the device to a PC or other computing device to store a composite record of many training sessions and view trend data. Such an embodiment is illustrated in FIG. 1. The present novel instantiation provides a wirelessly-networked, cloud-based system for continuously aggregating, analyzing, and displaying and notifying a trainee of the historical and real-time measurement data, as well as providing feedback on progress, training improvement suggestions, and honing sports performance. In this case, "wirelessly-networked" means a combination of wireless networks including a Personal Area Network (e.g. 802.15.4/ZigBee), a Local Area Network (e.g. 802.11/Wi-Fi), a Wide-Area network (e.g. 3G/4G Cellular), and possibly a Body Area Network (e.g. ANT). By "combination" we mean that the networks may be joined together to provide a composite network, for example BAN-to-PAN-to-WAN, or BAN-to-PAN-to-LAN. The BAN or PAN, for example, may link and multiplex data from a group of sensors, each of which is located at a different location on the body.

In some cases, the player or the patient is at one location where he or she performs movements measured by the sensors, while the coach or health care provider is at another location distant from the player or patient. In such cases, it may be inconvenient or difficult to communicate sensor measurements to the coach or healthcare provider resulting in delays in coaching instruction or diagnosis. The present disclosure addresses this and other problems.

Additionally, the use of wireless communication devices have become so prevalent in today's society that almost everyone uses a cell phone or other wireless communication device for communication with one another. As people become more confident with the use of these wireless communication devices and the services they provide, the use of wired devices, such as a wired telephone at home, have become less important in day-to-day life. The result of this change in behavior has led many people to discontinue their wired communication service and rely entirely on their wireless communication device. In some circumstances, such as those living on the fringe of service or living in large multi-unit complexes, the marginal signal strength in these locations makes relying entirely on a wireless service a somewhat risky proposition.

The above-described deficiencies of today's training regimens wireless communications systems are merely intended to provide an overview of some of the problems of conventional systems, and are not intended to be exhaustive. Other problems with the state of the art and corresponding benefits of one or more of the various non-limiting embodiments may become further apparent upon review of the following detailed description.

SUMMARY

The following presents a simplified summary of the specification in order to provide a basic understanding of some aspects of the specification. This summary is not an extensive overview of the specification. It is intended to neither identify key or critical elements of the specification nor delineate the scope of the specification. Its sole purpose is to present some concepts of the specification in a simplified form as a prelude to the more detailed description presented later.

The disclosure describes a system and methods for wirelessly monitoring sports activities. In one aspect, the system includes a system for monitoring sports activities, comprising: at least one sensor for continuously gathering biometric data from a subject performing a sports activity, the biometric data associated with the body movements of the subject; a wireless transceiver coupled to the at least one sensor for transmitting the biometric data; and a database engine for receiving the biometric data from the wireless transceiver and providing real-time feedback, wherein the real-time feedback associated with the biometric data from the subject is characterized by instructions associated with the sports activity.

In another aspect, the method includes a method for monitoring sports activities, comprising: continuously gathering biometric data from a subject performing a sports activity, the biometric data associated with the body movements of the subject; transmitting the biometric data at a transceiver; receiving the biometric data at a database engine; and providing real-time feedback associated with the biometric data from the subject, the real-time feedback characterized by instructions associated with the sports activity.

In another aspect, the system includes a system for monitoring the sports activities of a subject, comprising: at least one sensor for continuously gathering biometric data from a subject performing a sports activity, the biometric data associated with the body movements of the subject; a wireless transceiver coupled to the at least one sensor for transmitting the biometric data, the wireless transceiver including a display; and a database engine for receiving the biometric data from the wireless transceiver and providing real-time feedback, wherein the real-time feedback associated with the biometric data from the subject is characterized by instructions associated with the sports activity, and wherein the instructions associated with the sports activity are displayed in graphical form on the display.

Other systems, methods, and/or devices according to the exemplary embodiments will be or become apparent to one with skill in the art upon review of the following drawings and detailed description. It is intended that all such additional systems, methods, and/or devices be included within this description, be within the scope of the exemplary embodiments, and be protected by the accompanying claims.

BRIEF DESCRIPTION OF THE DRAWINGS

These and other features, aspects, and advantages of the exemplary embodiments are better understood when the following Detailed Description is read with reference to the accompanying drawings, wherein:

FIG. 10 is a flowchart illustrating the example steps according to exemplary embodiments.

DETAILED DESCRIPTION

Figure 1:
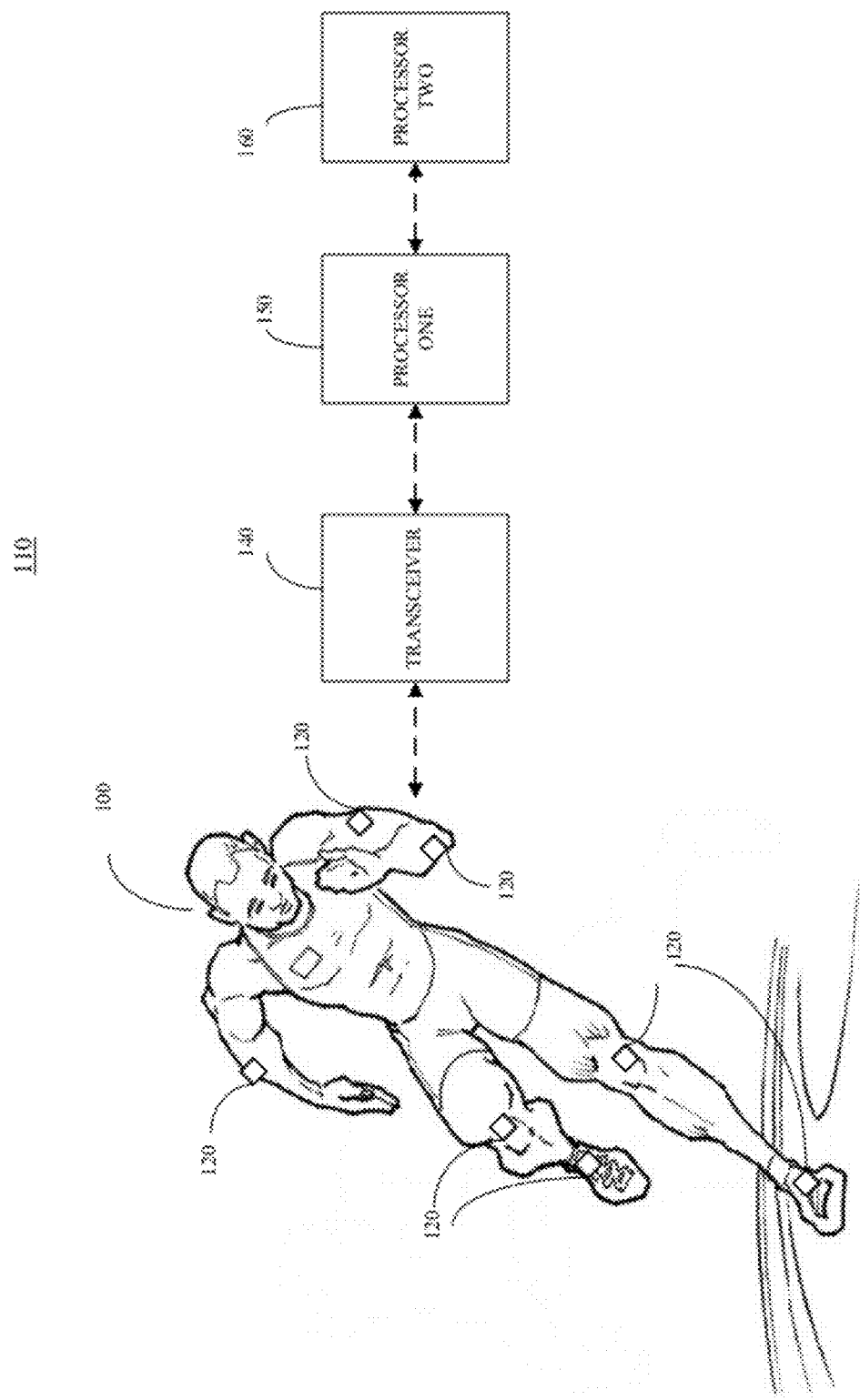
FIG. 1 is a simplified schematic illustrating an operating environment according to exemplary embodiments.

One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details, e.g., without applying to any particular networked environment or standard. In other instances, well-known structures and devices are shown in block diagram form in order to facilitate describing the embodiments in additional detail.

As used in this application, the terms "component," "module," "system," "engine," "interface," "platform," "station," "framework," "connector," or the like are generally intended to refer to a computer-related entity, either hardware, a combination of hardware and software, software, or software in execution or an entity related to an operational machine with one or more specific functionalities. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. As another example, an interface can include I/O components as well as associated processor, application, and/or API components.

Further, the various embodiments can be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications can be made to this configuration without departing from the scope or spirit of the various embodiments.

In addition, the words "exemplary" and "example" are used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, terms like "user equipment," "mobile station," "mobile," "subscriber station," "access terminal," "terminal," "handset," "end device," "mobile device," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "base station," "Node B," "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows.

Furthermore, the terms "user," "subscriber," "customer," and the like are employed interchangeably throughout the subject specification, unless context warrants particular distinction(s) among the terms. It should be appreciated that such terms can refer to human entities or automated components supported through artificial intelligence (e.g., a capacity to make inference based on complex mathematical formalisms), which can provide simulated vision, sound recognition and so forth. In addition, terms "core network", "core mobility network", "service provider network" and the like are employed interchangeably throughout the subject specification, unless context warrants particular distinction(s) among the terms.

The system and method described herein is used to measure and analyze data regarding various body movements, generally body movements performed in accordance with various sports activities. In one aspect, the data is conveyed wirelessly to a central server that provides real-time feedback to the user. The data is displayed to the user in conjunction with feedback which may convey information from a trainer, a coach, a doctor, or fellow competitors who may be remotely located from the location of the training or athletic activity. Data regarding the instantaneous measurement of the user's athletic performance may be monitored in the form of a graphical representation of the user's athletic performance.

In one aspect, the subject innovation can help prevent injury and improve athletic performance by enhancing confidence and providing diagnostic options and services to athletic participants. In another aspect, the subject innovation can enhance the training and competition for athletes whether they are beginners, amateurs, or professionals. The subject innovation may also foster the enjoyment of sports by beginners, amateurs and professional athletes. Embodiments disclosed herein can be used by consumers in various sports, industries, and market segments. Examples of suitable sports include, without limitation, golf, tennis, baseball, softball, football, soccer, track and field, running, jogging, walking, swimming, cycling, skateboarding, aerobics, yoga, weightlifting, bowling, volleyball, gymnastics, skiing, snowboarding. Indeed, the systems and methods described herein can be used in conjunction with any form of body movement, athletics, exercise, and/or recreation whether performed individually or in groups or teams The described technology and services are extendable across all sports platforms and into other areas such as medical devices, orthopedic medicine, military activities, law enforcement activities, aviation, space travel, and gaming.

A user can attempt to evaluate body movement data using a remote interface that can use digital performance assessment tools. In some aspects, the performance assessment and other data analysis can be accomplished whether the athlete, coach, or trainer are located proximate to each other or remotely located from each other. Thus, in some aspects, the described technology can provide a competitive edge to athletes, helping athletes perform better and/or reduce the possibility of injury. A preferred aspect can be used to monitor aspects of the athlete's performance and document the athlete's performance instantaneously during the athlete's performance. Real-time feedback may be provided by a trainer or a coach through a remote interface. In another aspect, the feedback may be provided by a database engine which instantaneously analyzes the body movement data and compares it to a predetermined metric or threshold. The engine can also correlate individual performance with statistical (anonymized) data to place the trainee with other trainees who have recorded training sessions (as a percentile, for example). In another aspect, the feedback may be provided through an interactive voice response ("IVR") which allows the subject to tune the feedback through hands-free operation. That is, the subject may control almost any function in the feedback interface by merely speaking through simple menu choices.

In some aspects, the innovation described herein allows for use of data gathered through such a system. The data from multiple users can be gathered and used for research, medical diagnosis, establishment of norms, averages, baselines, aberrations, standards for athletic recruiting, calibrations, etc. An archival log of a database of body movement data can be advantageous for these and various purposes.

Referring to the drawings, FIG. 1 illustrates an example system 110 for processing data from biometric and biomechanical sensors. A subject 100 has various biometric and biomechanical sensors 120 positioned on the subject's body. The sensors 120 may be attached to the subject's clothing or shoes or may be woven or positioned with the subject's clothing or shoes. In one aspect, the sensors 120 can be associated with joints and appendages of the body in order to track position and or movement of such joints and appendages. The sensors 120 can gather data relating to various physical characteristics, positions, changes, performance, or properties of the subject. This data can be referred to as "biometric" data. Biometric data includes biomedical and biomechanical data, and can include any of the following: data tracing the trajectory, speed, acceleration, position, force/pressure exerted by or experienced by the body, orientation, etc. of a subject's appendage or other body part; data showing the heart rate, blood pressure, temperature, stress level, moisture content, toxin level, viability, respiration rate, etc. of a subject; data showing whether or not a subject is performing a signal or communication movement (e.g., teeth closed, arm cocked, etc.); data showing the posture or other status of a subject (e.g., prone or erect, breathing or not, moving or not); data showing the emotional state of a subject; etc. For example, the sensors can track movement of the subject and/or tension in the subject's muscles. In some embodiments, the sensors 120 can include one or more of the following technologies: accelerometer technology that detects accelerations; gyroscope technology that detects changes in orientation; compass or magnetic technology that senses position and/or alignment with relation to magnetic fields; satellite-based; "GPS"-style technology; gait or stride instabilities or impact points; radio-frequency technology, etc.

The sensors 120 communicate with a transceiver 140. In one aspect, the transceiver can be attached to the body and/or clothing (for e.g., the belt) of the subject 100. The transceiver 140 can collect and store data (e.g., analog and/or digital data) from the sensors 120. In one aspect, the data is converted from analog to digital in the sensors or the transceiver to facilitate storage and/or transmittance. In another aspect, the data is sequenced, coded, and or separated to make the reception, storage, and/or transmission more efficient through compression of the data or the like. In some embodiments, the transceiver 140 can be a mobile device, a cell phone, smartphone, personal digital assistant (PDA), pocket PC, tablet PC, MP3 player, or other portable communications and/or computing device. The mobile device may be a disposable cell phone or a prepaid cell phone. In some aspects, the transceiver 140 can send signals to and/or receive signals from a portable communications device such as those mentioned here, for example.

The transceiver 140 can transmit data to a first processor 150. The data can be transmitted in electronic or electromagnetic form, for example. In some aspects, the data is transmitted wirelessly (using radio frequency transmissions, for example). Various communications protocols can be used, including, for example, Bluetooth, ZigBee, TCP/IP, 802.11b, 802.11a, 802.11g, 802.11e, etc.). In some aspects, the transceiver 140 transmits the data over the internet or over a wired or wireless network.

The first processor 150 can be one of or a combination of devices or components. In some aspects, the first processor 150 can be a computer and/or remote server such as a laptop computer or computer chip/ASIC, for example. The first processor 150 can be configured to receive signals from the transceiver 140 and can have software that allows a user to view or otherwise use the data. In some aspects, the first processor 150 can be a mobile device, a cell phone, smartphone, personal digital assistant (PDA), pocket PC, tablet PC, MP3 player, or other portable communications and/or computing device. In some aspects, the functions described for the transceiver 140 and the first processor 150 can be merged into a single device. Therefore, a single portable communications device can be configured to variously collect data from the sensors 120; store the data in its onboard memory (or on a portable storage such as a memory card), and transmit the data. In some aspects, the data transmission continues to a second processor 160.

In one aspect, the subject may access the biometric data from the sensors concurrent with the transmission to the second processor. Therefore, in some aspects, the subject 100 can gather physiological and/or biometric data using the sensors 120, send that data to the transceiver 140 which in turn transmits the data to the first processor 150, which can be the subject's laptop, for example. The subject can then become a user of the biometric data by accessing the data from the first processor. It is contemplated that the user can view or interact with the data in a variety of formats. For example, in one aspect, the primary feedback method to the subject is auditory: The wireless link would use speech synthesis to create a "narrative" of data, progress, and warnings (e.g. high-pulse rate). This notification function can also provide "reassurance" that the network is functional and is collecting/analyzing data (e.g. a periodic "beep" indicating that data is being received by the database/analyzer). This prevents the irritation of starting a training or competitive session with a failing battery in one or more of the sensors, wireless radios, etc. In another example, the user can view three-dimensional animations, histograms, or other graphical reports of the subject's athletic performance. As a further example, the user can view the data in a tabular format so that the data may be compared to the subject's past performance metrics (for e.g., against the subject's best past performances, average performances, performances in similar environmental conditions, or the like). As a further example, the user can view the data in a tabular format so that the data may be compared to metrics observed in other competitors' athletic performances. In a preferred aspect, the data collected by the sensors permit the subject user to view an animation of the user's own movements as reconstructed from the biomechanical data collected by the sensors. Additionally, in some aspects, the user can view animations of another person's movements reconstructed from biomechanical data collected on the other person's movements. As another example, the user can view his or her own performance and then view animation of the performance of a friend, coach, competitor, instructor, trainer, or professional. It will be understood that the user can then be an athlete, patient, coach, doctor, physical therapist, parent, data analyst, etc., and need not be the same entity as the subject 100. As a further example, various means of presenting the tracking information in a visual display may be employed, such as Heads-Up Display (HUD), that provide occluded or see-through visibility of the physical world, or Fixed-Surface Display (FSD), such as computer desktop monitors, depending upon the simulation and immersive quality required for the application. The application may require various degrees of aural, visual, and tactile simulation fidelity and construct direct or composite camera views of the augmented or three dimensional (3D) virtual reality environment to elicit interactive user locomotion and/or object manipulation to enhance the user's performance and perception therein. The tracked object may be represented in the virtual environment in various forms, i.e., as a fully articulated anthropoid or depicted as a less complex graphical primitive.

As previously mentioned, the data can be sent from the first processor 150 to a second processor 160 (e.g., via a wired or wireless network or the internet, for example). In some aspects, the second processor 160 can perform the functions described above with respect to the first processor 150. In some other aspects, the second processor 160 can perform additional analysis or processing. As shown in FIG. 1, the second processor, in some aspect, can make the data available to a second user. The second user can be the subject 100 and/or the first user 152, but the second user can also be a different entity such as a specialist, statistician, analyst, doctor, or coach, or the like. In a preferred aspect, the second user 162 can communicate or interact with the first user. Therefore, the second user (for e.g., a coach) can have access to the same data being viewed by the first user and/or subject 100 such as an athlete. The second user can then interpret and explain the data to the subject 100, request more data, use automated analysis methods (e.g., using the second processor 160) to extract diagnostic information from the data, speak or send further information to the first user. In this way, the second user can provide a "virtual" instruction or training to the subject 100 regarding the subject's body movements (e.g., golf swing, baseball pitch, running stride, gait, tennis swing, swimming stroke, rehabilitative movement, etc.).

It is contemplated that additional users and additional processors can be used. As an example, a third user can comprise an institution that collects data from multiple subjects or multiple users and processes that data to find patterns or establish norms, for example. In some aspects, the system can comprise sports training monitoring equipment that allows an athlete and/or trainer to monitor an individual training program and to compare an exercise program to a previously stored reference workout or other benchmark. An athletic trainer can monitor an athlete workout in real time by monitoring sensor data captured and wirelessly transmitted to the trainer display system. As used herein, the term "real time" is used broadly to mean that the data is not available hours later, but is instead available within less than one hour. In a preferred aspect, the monitoring and some analysis can be done instantaneously. Advantageously, high-speed data transfer can allow monitoring to occur within a short time (e.g., less than 5 minutes) of the body movement. In some aspects, monitoring can occur within less than one minute of the body movement. In one aspect, all data is stored so that analysis of that data can be compared to other athletes and enhance the training programs, automatically alerting a central network monitoring authority, with associated components is illustrated in accordance with aspects described herein.

Various other analysis of the subject's athletic performance are contemplated. For example, applications may include a Competitive Ranking. Competitive Ranking applications such as a predominantly point goal-oriented purpose would allow access to a global ranking file archive accessed through the Internet or automatically via updated executive files. This ranking file would be created through an analysis of user participation and publishing of his/her results through Internet Web-based services.

Another example is a Downloadable Executive Program which includes graphics images would be stored in compressed or uncompressed binary forms, i.e., bitmap, gif, jpeg, etc. This new programs could be transferred to any suitable computerized position processor unit located at a remote facility via the transponder's wireless link. Therefore, the user's transponder is the node that establishes the portable network capabilities of the system, not necessarily the computerized position processor.

Custom Menu Interfaces allow a subject or a trainer or coach to customize the interface so that specialized athletic activities may require more advanced (or simplified) interfaces dependent upon the users' cognitive abilities and interactive specificity. This menu may include interactive queries or solicit information regarding the user's daily goals, subjective opinions or overall impression of the activity and one's performance which could be incorporated in the Motivation Index described below.

Various other Report Generation Tools and Templates are also contemplated. XML, HTML or other authoring language used to create documents on the Web that would provide an interactive browser-based user interface to access additional performance data analysis and report generation tools and templates that may not be available or offered with the standard product.

A Custom Performance Algorithm can include a performance analysis which is specifically tailored to the athlete and the particular sport or activity. Certain application-specific performance analysis may require dynamically linked algorithms that process and calculate non-standard or specialized information, values, units, physical measurements, statistical results, predictive behaviors, filtering, numerical analysis including differentiation and integration, convolution and correlation, linear algebraic matrices operations to compute data pose and scaling transformation, and proprietary types. One example of a proprietary type is Motivation Index, a composite numerical value derived from a weighted average of statistical performance indicators and subjective user input including relative scoring improvements, conformity to ROM pattern, lengthy activity access duration, high access rate, relative skill level improvement, daily goal achievement, etc., that could represent the overall level of enthusiasm and satisfaction, the user has for a particular activity.

As a further example, a Range of Motion (ROM) Pattern Generator provides key control points to be captured along the desired trajectory and stored in order that the algorithm can calculate an optimally smooth path, in real-time, during the comparative analysis phase. A further example is a ROM Pattern Capture & Replay so that the athlete can replay the performance. The ROM pattern can be can saved to memory in real-time by discrete position samples versus time depending upon the resolution desired and memory limitations and later played back on the transponder or remote display for analysis.

It is contemplated that other Activity Specific Attributes, including Reps/Sets, Duration, Pause, Heart Rate Limits, intra-activity delay, level, point scalars, energy expenditure, task-oriented triggers, etc., and other parametric data that controls intensity, execution rate and scoring criteria for the activity may also be measured and analyzed.

An exemplary sensor 120 is a sensor utilized for biomechanics and gait analysis. The gait sensor allows for the capturing of a subject's gait pattern. A gait sensor may include a tread plate supported in a frame via an elastic suspension that will be described hereafter in more detail, with one or more sensors 5 (see FIG. 4)—configured as acceleration sensors in this case—arranged below that suspension, motion capture, or performance animation and require the sensors to be precisely mounted on the joints. Various means of presenting the tracking information in a visual display are employed, such as Heads-Up Display (HUD), that provide occluded or see-through visibility of the physical world, or Fixed-Surface Display (FSD), such as computer desktop monitors, depending upon the simulation and immersive quality required for the application. The application may require various degrees of aural, visual, and tactile simulation fidelity and construct direct or composite camera views of the augmented or three dimensional (3D) virtual reality environment to elicit interactive user locomotion and/or object manipulation to enhance the user's performance and perception therein. The tracked object may be represented in the virtual environment in various forms, i.e., as a fully articulated anthropoid or depicted as a less complex graphical primitive. The rendering strategy employed depends upon the degree of photo realism required with consideration to its computational cost and the application's proprioception requirements.

Figure 2:
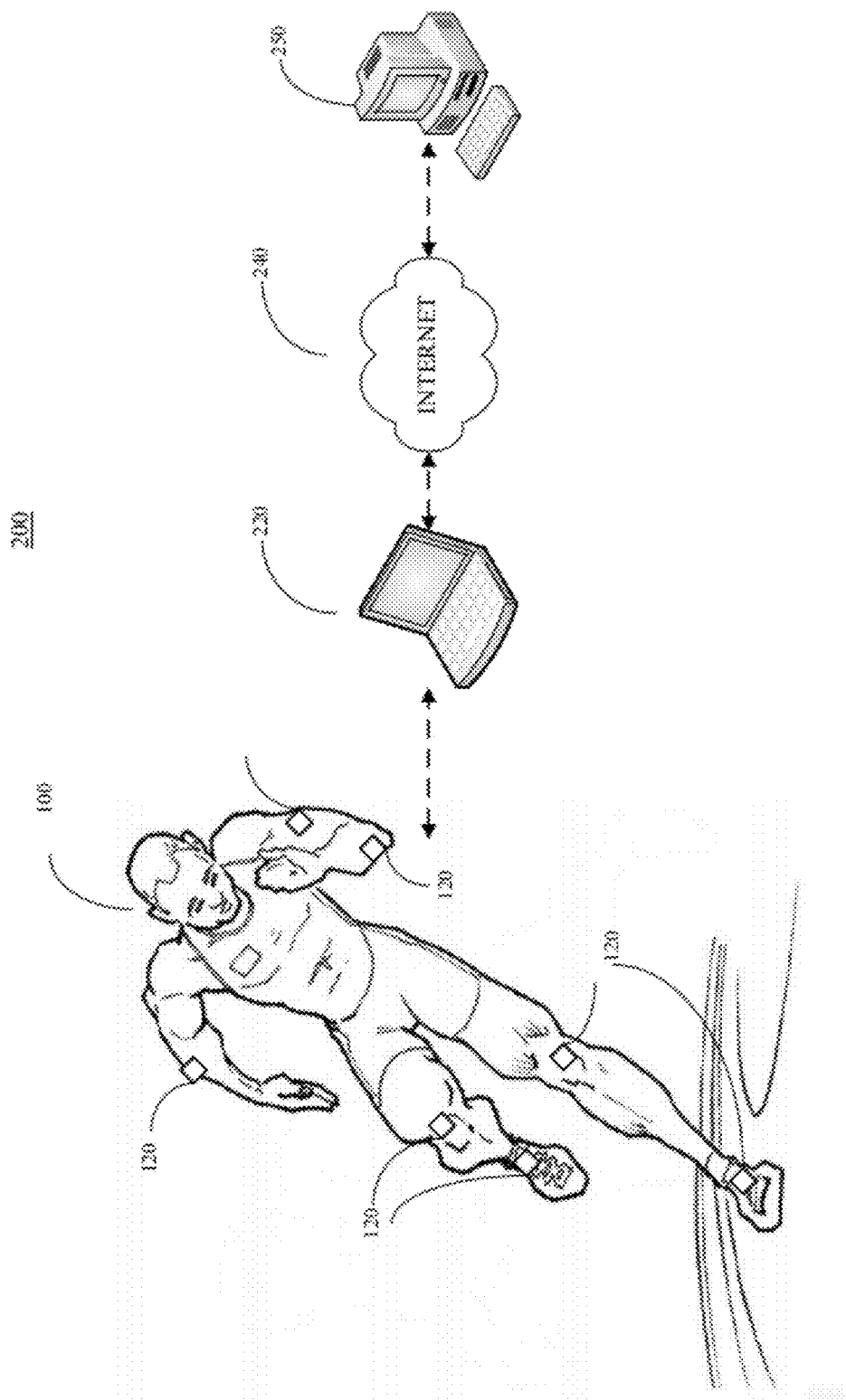
FIG. 2 is a simplified schematic illustrating an operating environment according to exemplary embodiments.

Referring to FIG. 2, there is shown a schematic diagram of a system 200 in accordance with an exemplary embodiment. The system 200 shows a track and filed athlete 100 as the subject with various sensors 120 positioned on the athlete's body. It will be understood that the sensors 120 can also be woven into the fabric of the clothing. In another aspect, the sensors can be incorporated into an undergarment so they are less noticeable and/or cumbersome and conform more closely to the user's body. In some aspects, sensors can be embedded in the skin of a user. The sensors 120 can gather data relating to the subject's form, balance, gait, speed, position, and/or stride. The sensors 120 can then send data to a transceiver (not shown).

The transceiver may have a clip for attaching to a belt, for example. The clip can rotate in order to allow the transceiver to be oriented in various ways, according to the needs or the whim of the athlete. The transceiver whim of the golfer 121. The transceiver may be connected to the various sensors 120 by wires or leads (not shown). In a preferred aspect, the transceiver can gather data from the various sensors 120 by a wireless connection. In some aspects, the data is transmitted wirelessly (using radio frequency transmissions, for example). Various communications protocols can be used, including, for example, Bluetooth, ZigBee, TCP/IP, 802.11b, 802.11a, 802.11g, 802.11e, etc.).

The transceiver forwards the data wirelessly to a laptop computer 220 (which is an example of a device that can act as the first processor 150 of FIG. 1). In some aspects, the transceiver can transmit data wirelessly via the internet. In another aspect, the transceiver can store data on its onboard memory (or a memory card) for later transfer to a first processor. In a preferred aspect, the transceiver is a some embodiments, the transceiver is a mobile device, a cell phone, smartphone, personal digital assistant (PDA), pocket PC, tablet PC, MP3 player, or other portable communications and/or computing device. The mobile device may be a disposable cell phone or a prepaid cell phone. In some aspects, the transceiver 140 can send signals to and/or receive signals from a portable communications device such as those mentioned here, for example.

As the data is transferred to the laptop computer 220, appropriate software on the laptop computer 220 analyzes the data and may provide a graphical evaluation of the athlete's performance with graphs, numbers, graphical depictions, charts, histograms, etc. The performance evaluation can include statistical analyses that, for example, determine the user's average performance level and the user's deviations from this average. For example, statistical techniques can be used to compare the user's performance level with other suitable athletes as defined by demographics, geography, performance level, etc. Statistical analyses may also enable a coach to track the performance of a particular player on a team as compared to other team members, selected past teams, competitor teams, professional teams, etc. The data relating to a particular performance by the athlete can be referred to as a "performance fingerprint," and can have unique characteristics. The performance fingerprint can be sent from the laptop computer 220 to another computer such as a desktop computer 150 (an example of the second processor 160 of FIG. 1). This data transmission may occur through the internet 240 or some other suitable network. It will be understood that, in some aspects, a mobile device, a cell phone, smartphone, personal digital assistant (PDA), pocket PC, tablet PC, MP3 player, or other portable communications and/or computing device may supplement, or in some cases, be used in lieu of the laptop computer 220 described herein. For example, a cell phone, PDA, etc. can upload data to the World Wide Web, and that data (in raw or processed form) can also be accessed from the cell phone, PDA, etc. In some aspects, a user's data can be sent to a "learning center" via the World Wide Web, and then that same user can thereafter access charts, histograms, etc. that are visible on that user's cell phone, PDA, etc. that provide insight to the user relating to the data and/or the user's performance.

In some aspects, the data can be viewed and/or analyzed by a third party or the subject. For example, in one aspect, the data is displayed and played back at a later time by the subject in order to relive the training experience. The desktop computer 250 can be located at a centralized data processing location where a coach, a trainer, or physical therapist can look at the data and assist the athlete 100 in understanding the performance fingerprint or provide real-time feedback. The desktop and/or third party can provide a "remote performance evaluation" to the athlete. The data from the athlete's performance can also be stored in raw and/or processed form for later analysis and comparison.

Figure 3:
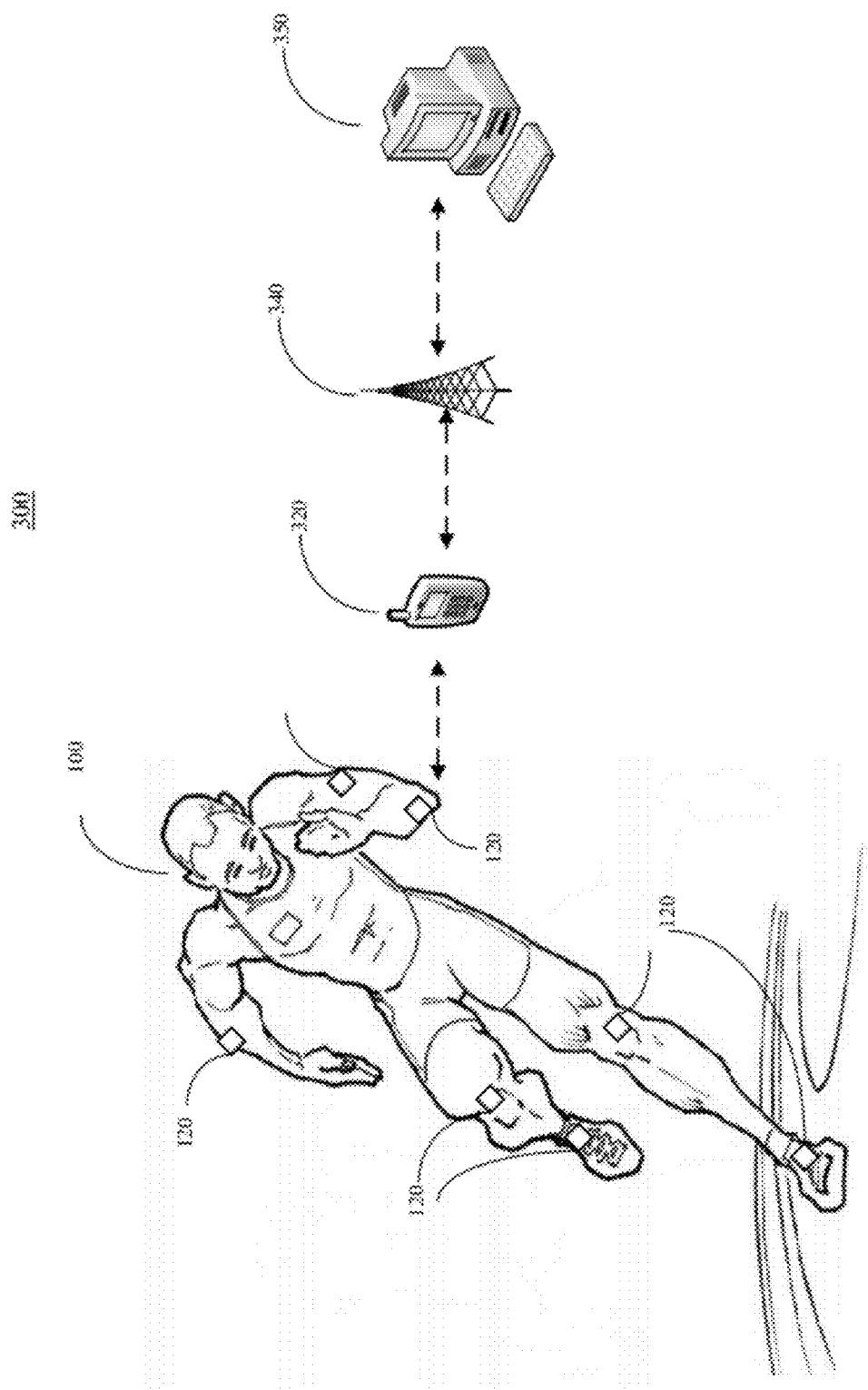
FIG. 3 is a simplified schematic illustrating an operating environment according to exemplary embodiments.

FIG. 3 shows another aspect of a system 300 in accordance with an exemplary embodiment. The system 300 shows a track and filed athlete 100 as the subject with various sensors 120 positioned on the athlete's body. It will be understood that the sensors 120 can also be woven into the fabric of the clothing. In another aspect, the sensors can be incorporated into an undergarment so they are less noticeable and/or cumbersome and conform more closely to the user's body. In some aspects, sensors can be embedded in the skin of a user. The sensors 120 can gather data relating to the subject's form, balance, gait, speed, position, and/or stride. The sensors 120 can then send data to a transceiver (not shown).

The transceiver may have a clip for attaching to a belt, for example. The clip can rotate in order to allow the transceiver to be oriented in various ways, according to the needs or the whim of the athlete. The transceiver whim of the golfer 121. The transceiver may be connected to the various sensors 120 by wires or leads (not shown). In a preferred aspect, the transceiver can gather data from the various sensors 120 by a wireless connection. In some aspects, the data is transmitted wirelessly (using radio frequency transmissions, for example). Various communications protocols can be used, including, for example, Bluetooth, ZigBee, TCP/IP, 802.11b, 802.11a, 802.11g, 802.11e, etc.).

The transceiver forwards the data wirelessly to a mobile device 320 (which is an example of a device that can act as the first processor 150 of FIG. 1). In some aspects, the transceiver can transmit data wirelessly via the internet. In another aspect, the transceiver can store data on its onboard memory (or a memory card) for later transfer to a first processor. In a preferred aspect, the transceiver is a some embodiments, the transceiver is a mobile device, a cell phone, smartphone, personal digital assistant (PDA), pocket PC, tablet PC, MP3 player, or other portable communications and/or computing device. The mobile device may be a disposable cell phone or a prepaid cell phone. In some aspects, the transceiver can send signals to and/or receive signals from a portable communications device such as those mentioned here, for example.

In some aspects, the functions described for the transceiver and the mobile device 320 can be merged into a single device. Therefore, a single portable communications device can be configured to variously collect data from the sensors 120; store the data in its onboard memory (or on a portable storage such as a memory card), and transmit the data. In some aspects, the data transmission continues to a second processor 350.

As the data is transferred to the mobile device 320, appropriate software on the mobile device 320 analyzes the data and may provide a graphical evaluation of the athlete's performance with graphs, numbers, graphical depictions, charts, histograms, etc. The performance evaluation can include statistical analyses that, for example, determine the user's average performance level and the user's deviations from this average. For example, statistical techniques can be used to compare the user's performance level with other suitable athletes as defined by demographics, geography, performance level, etc. Statistical analyses may also enable a coach to track the performance of a particular player on a team as compared to other team members, selected past teams, competitor teams, professional teams, etc. The data relating to a particular performance by the athlete can be referred to as a "performance fingerprint," and can have unique characteristics. The performance fingerprint can be sent from the mobile device 320 to another computer such as a desktop computer 350 (an example of the second processor 160 of FIG. 1). This data transmission may occur through the wireless network 340 or some other suitable network. It will be understood that, in some aspects, the mobile device may be a cell phone, smartphone, personal digital assistant (PDA), pocket PC, tablet PC, MP3 player, or other portable communications and/or computing device may supplement, or in some cases, be used in lieu of the mobile device 320 described herein. For example, a cell phone, PDA, etc. can upload data to the World Wide Web, and that data (in raw or processed form) can also be accessed from the cell phone, PDA, etc. In some aspects, a user's data can be sent to a "learning center" via the World Wide Web, and then that same user can thereafter access charts, histograms, etc. that are visible on that user's cell phone, PDA, etc. that provide insight to the user relating to the data and/or the user's performance.

In some aspects, the data can be viewed and/or analyzed by a third party. The desktop computer 350 can be located at a centralized data processing location where a coach, a trainer, or physical therapist can look at the data and assist the athlete 100 in understanding the performance fingerprint or provide real-time feedback. The desktop and/or third party can provide a "remote performance evaluation" to the athlete. The data from the athlete's performance can also be stored in raw and/or processed form for later analysis and comparison.

Figure 4:
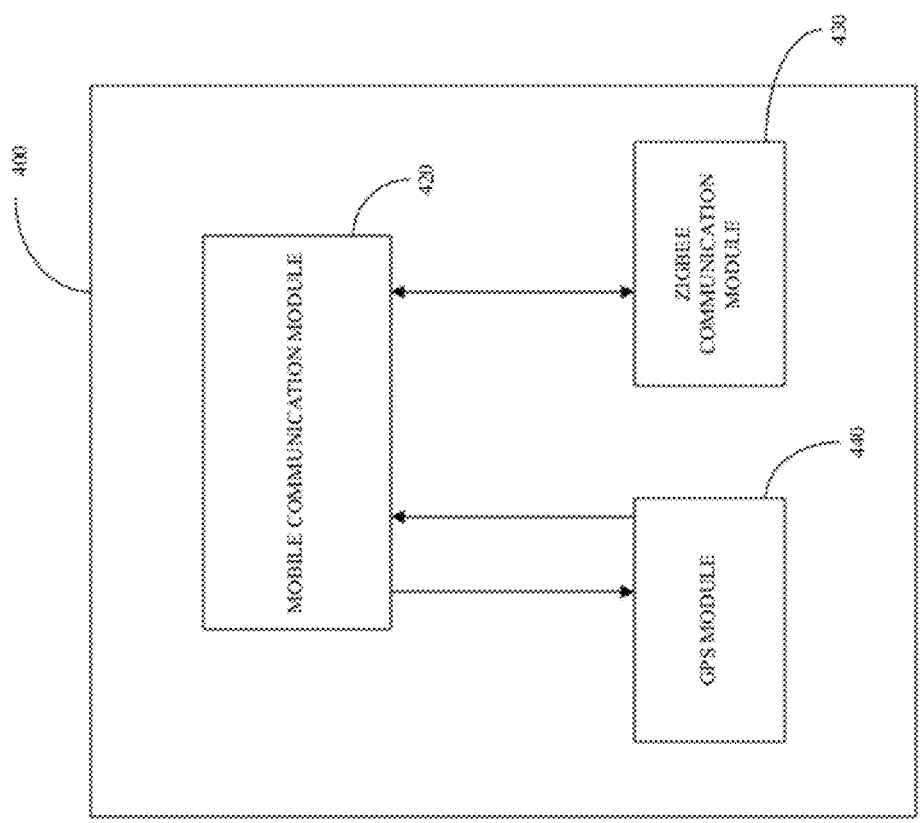
FIG. 4 is a simplified schematic illustrating a mobile device according to exemplary embodiments.

Referring to FIG. 4, there is shown a schematic diagram of a mobile device 400 which is particularly suited for combining the transceiver and first processor functions. The mobile device 400 includes a Zigbee communication module 430 for executing a Zigbee communication according to IEEE 802.15.4 standards, a global positioning system (GPS) module 440 obtaining the position data of the mobile device, and a mobile communication module 420 for communicating on the wireless network. In a preferred aspect, the Zigbee communication protocol is particularly suited for use with low-power sensors.

Zigbee wireless network communication protocol suite is based on the IEEE 802.15.4 standard and typically operates at the globally available 2.4 GHz bandwidth and provide a data rate of 250 Kbits/second. Zigbee is a low-cost, low-power, wireless mesh networking standard which affords a number of advantages. The low cost allows the technology to be widely deployed in wireless control and monitoring applications. Further, the low power-usage allows longer life with smaller batteries. Additionally, the mesh networking provides high reliability and more extensive range.

The Zigbee communication module interacts with the GPS module. The GPS module generates GPS reference signals, and a GPS module embedded in each mobile device for receiving and processing these GPS reference signals. In one aspect, the GPS module provides positioning/location/altitude information which may aid in the training of the athlete 100. For example, a track and field athlete or runner may incorporate altitude training and/or gauge his or her speed on the uphill climbing portion of the training run versus the downhill portion of the training run.

Figure 5:
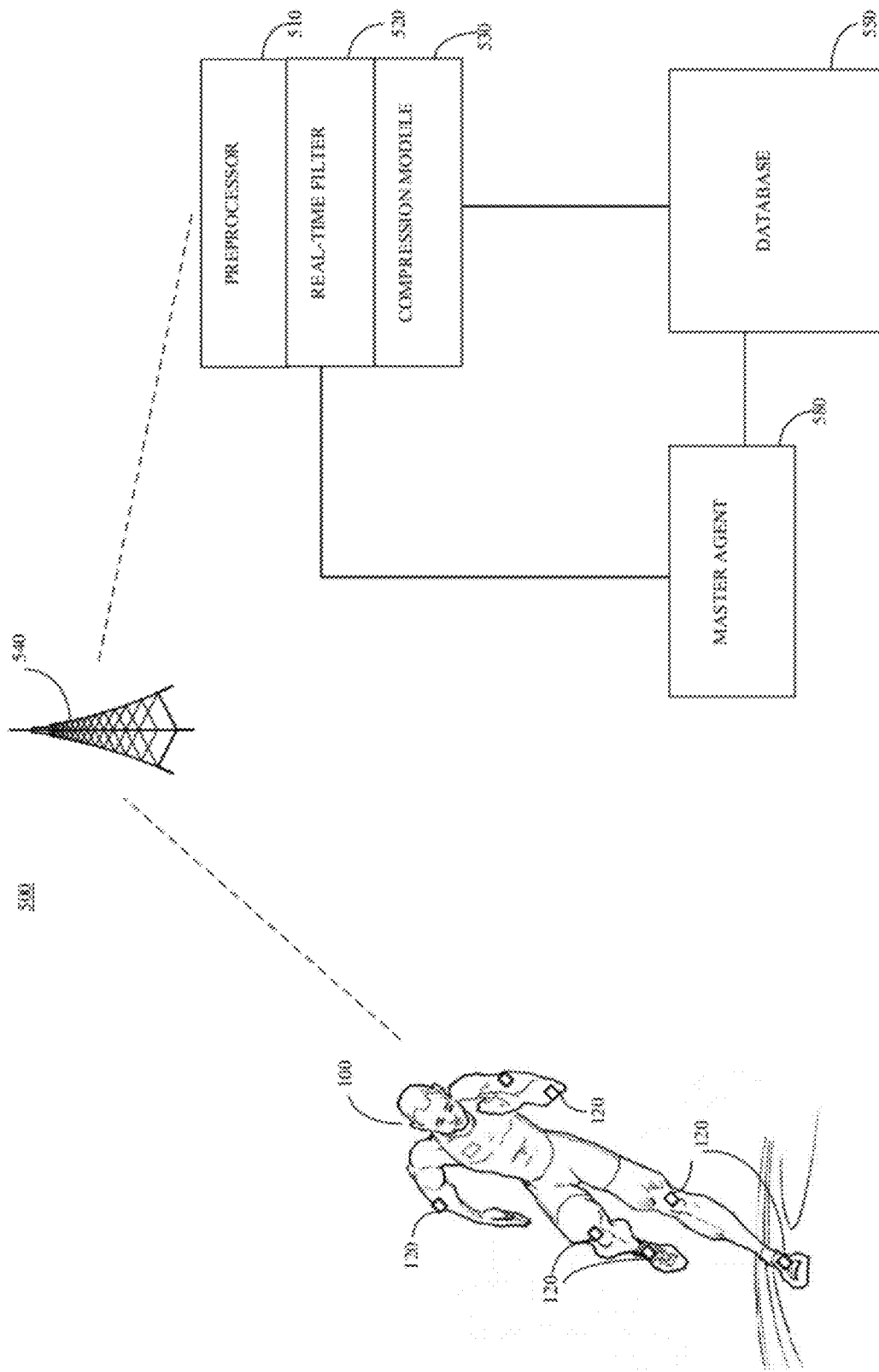
FIG. 5 is a simplified schematic illustrating an operating environment according to exemplary embodiments.

FIG. 5 is a schematic diagram in accordance with an exemplary embodiment of the system. The subject 100 has various biometric and biomechanical sensors 120 positioned on the subject's body. The sensors 120 may be attached to the subject's clothing or shoes or may be woven or positioned with the subject's clothing or shoes. In one aspect, the sensors 120 can be associated with joints and appendages of the body in order to track position and or movement of such joints and appendages. The sensors 120 can gather data relating to various physical characteristics, positions, changes, performance, or properties of the subject. This data can be referred to as "biometric" data. Biometric data includes biomedical and biomechanical data, and can include any of the following: data tracing the trajectory, speed, acceleration, position, orientation, etc. of a subject's appendage or other body part; data showing the heart rate, blood pressure, temperature, stress level, moisture content, toxin level, viability, respiration rate, etc. of a subject; data showing whether or not a subject is performing a signal or communication movement (e.g., teeth closed, arm cocked, etc.); data showing the posture or other status of a subject (e.g., prone or erect, breathing or not, moving or not); data showing the emotional state of a subject; etc. For example, the sensors can track movement of the subject and/or tension in the subject's muscles. In some embodiments, the sensors 120 can include one or more of the following technologies: accelerometer technology that detects accelerations; gyroscope technology that detects changes in orientation; compass or magnetic technology that senses position and/or alignment with relation to magnetic fields; satellite-based, "GPS"-style technology; radio-frequency technology; etc.

The sensors 120 communicate with a transceiver (not shown). In one aspect, the transceiver can be attached to the body and/or clothing (for e.g., the belt) of the subject 100. The transceiver collects and store data (e.g., analog and/or digital data) from the sensors 120. In one aspect, the data is converted from analog to digital in the sensors or the transceiver to facilitate storage and/or transmittance. In another aspect, the data is sequenced, coded, and or separated to make the reception, storage, and/or transmission more efficient through compression of the data or the like. In some embodiments, the transceiver can be a mobile device, a cell phone, smartphone, personal digital assistant (PDA), pocket PC, tablet PC, MP3 player, or other portable communications and/or computing device. The mobile device may be a disposable cell phone or a prepaid cell phone. In some aspects, the transceiver can send signals to and/or receive signals from a portable communications device such as those mentioned here, for example.

The transceiver can transmit data to the wireless network 540. The data can be transmitted in electronic or electromagnetic form, for example. In some aspects, the data is transmitted wirelessly (using radio frequency transmissions, for example). Various communications protocols can be used, including, for example, Bluetooth, Zigbee, TCP/IP, 802.11b, 802.11a, 802.11g, 802.11e, etc.). In some aspects, the transceiver transmits the data over the internet or over a wired or wireless network.

The data is transmitted for storage and analysis to the database 550. A preprocessor 510 first receives the data so that various noises are removed from the data resulting in a data with a higher signal to noise ratio. In one aspect, the preprocessor 510 extracts identifiable features from the data so that windowing, sub-band transformation, mean extraction, and re-sampling may be prioritized in the extraction of data from the signal.

A real-time filter 520 then extracts or filters out data that may be necessary for archival or historical purposes from the necessary data for real-time analysis. In one aspect, the filter 520 produces a result, typically based on the entire record, based on access records which are typically not applied in athletic training. For example, if the subject is a golfer, pulse-monitoring data may not be authorized or inappropriate for analysis by a golf swing coach. The real-time filter 520 applies access rules so that unauthorized data is not accessible to inappropriate personnel. In another aspect, the filter applies rule validation and administration for firewalls. Filter rules on a firewall between a secure computer network and a nonsecure computer network are validated from a user interface. A user interface is presented in which a test packet can be defined. The user interface includes controls for defining values for attributes of the test packet, wherein the attributes of the test packet are selected from a set of attributes of normal packets normally sent between the secure and nonsecure computer networks. A defined test packet is validated against a set of filter rules in the firewall or matched against the filter rules to determine those filter rules with matching attributes to the defined packet. When validating, responsive to the failure of the test packet in the validating step, the filter rule in the set of filter rules that denied the test packet is displayed to the data is since the access rules are typically not applied within the custodian network. The results must then be filtered based on the defined rules.

The data is then transmitted to the compression module 530. The compression module 530, in one aspect, applies an efficient data compression/decompression scheme using a passive data storage media for storage of athletic performance information. The system operates on central processing hardware so that efficient storage and retrieval of information may be provided.

The database 550 is a highly structured data storage which provides for transmission, use and security protection of the data. In one aspect, the database is a key management system wherein a plurality of keys are stored in a secure key database. A user authentication, such as a biometric authentication, is used to access the secure key database. Often the database is encrypted with a key that is accessible through user authentication.

In another aspect, the database 550 is a biometric and biomechanical data services provider (e.g., the provider of the sensors, the operator of a website, the server, the storage systems, and the database 1520) can collect, store, and mine any of the acquired biometric data for any suitable instructional, health-related, marketing, promotional, advertising, or business objective. The biometric data can be shared among doctors, trainers, and health professionals to develop new methods to prevent or reduce injury or to help improve recovery from injury. It will be apparent that many types of devices and many wired and wireless channels of communication are possible to share biometric and biomechanical data derived from one or more sensors 120 among various users, learning centers, websites, etc. Many uses are possible and the examples discussed herein are intended to be illustrative and non-limiting.

The master agent 580 provides feedback to the athlete and acts as a "virtual" trainer or coach. In the absence of a human coach or trainer (or as a supplement thereto), the master agent analyzes the data instantaneously and provides statistical analysis and real-time feedback to the athlete. For example, the master agent collects data from multiple subjects or multiple users and processes that data to find patterns or establish norms. In some aspects, the master agent can include rules based analysis so that an individual training program is analyzed and compared to an exercise program to a previously stored reference workout or other benchmark. As a further example, the master agent can monitor an athlete workout in real time by monitoring sensor data captured and wirelessly transmitted to the trainer display system. As used herein, the term "real time" is used broadly to mean that the data is not available hours later, but is instead available within less than one hour. In a preferred aspect, the monitoring and some analysis can be done instantaneously. Advantageously, high-speed data transfer can allow monitoring to occur within a short time (e.g., less than 5 minutes) of the body movement. In some aspects, monitoring can occur within less than one minute of the body movement. In one aspect, all data is stored so that analysis of that data can be compared to other athletes and enhance the training programs automatically alerting a central network monitoring authority, with associated components is illustrated in accordance with aspects described herein.

Various other analysis of the subject's athletic performance are contemplated. For example, the master agent may apply an application for Competitive Ranking. Competitive Ranking applications such as a predominantly point goal-oriented purpose would allow access to a global ranking file archive accessed through the Internet or automatically via updated executive files. This ranking file would be created through an analysis of user participation and publishing of his/her results through Internet Web-based services.

Another example is a Downloadable Executive Program which includes graphics images would be stored in compressed or uncompressed binary forms, i.e., bitmap, gif, jpeg, etc. This new programs could be transferred to any suitable computerized position processor unit located at a remote facility via the transponder's wireless link. Therefore, the user's transponder is the node that establishes the portable network capabilities of the system, not necessarily the computerized position processor.

Custom Menu Interfaces allow a subject or a trainer or coach to customize the interface so that specialized athletic activities may require more advanced (or simplified) interfaces dependent upon the users' cognitive abilities and interactive specificity. This menu may include interactive queries or solicit information regarding the user's daily goals, subjective opinions or overall impression of the activity and ones performance which could be incorporated in the Motivation Index described below.

Various other Report Generation Tools and Templates are also contemplated. XML, HTML or other authoring language used to create documents on the Web that would provide an interactive browser-based user interface to access additional performance data analysis and report generation tools and templates that may not be available or offered with the standard product.

A Custom Performance Algorithm can include a performance analysis which is specifically tailored to the athlete and the particular sport or activity. Certain application-specific performance analysis may require dynamically linked algorithms that process and calculate non-standard or specialized information, values, units, physical measurements, statistical results, predictive behaviors, filtering, numerical analysis including differentiation and integration, convolution and correlation, linear algebraic matrices operations to compute data pose and scaling transformation, and proprietary types. One example of a proprietary type is Motivation Index, a composite numerical value derived from a weighted average of statistical performance indicators and subjective user input including relative scoring improvements, conformity to ROM pattern, lengthy activity access duration, high access rate, relative skill level improvement, daily goal achievement, etc., that could represent the overall level of enthusiasm and satisfaction, the user has for a particular activity.

As a further example, a Range of Motion (ROM) Pattern Generator provides key control points to be captured along the desired trajectory and stored in order that the algorithm can calculate an optimally smooth path, in real-time, during the comparative analysis phase. A further example is a ROM Pattern Capture & Replay so that the athlete can replay the performance. The ROM pattern can be can saved to memory in real-time by discrete position samples versus time depending upon the resolution desired and memory limitations and later played back on the transponder or remote display for analysis.

It is contemplated that other Activity Specific Attributes, including Reps/Sets, Duration, Pause, Heart Rate Limits, intra-activity delay, level, point scalars, energy expenditure, task-oriented triggers, etc., and other parametric data that controls intensity, execution rate and scoring criteria for the activity may also be measured and analyzed.

Figure 6:
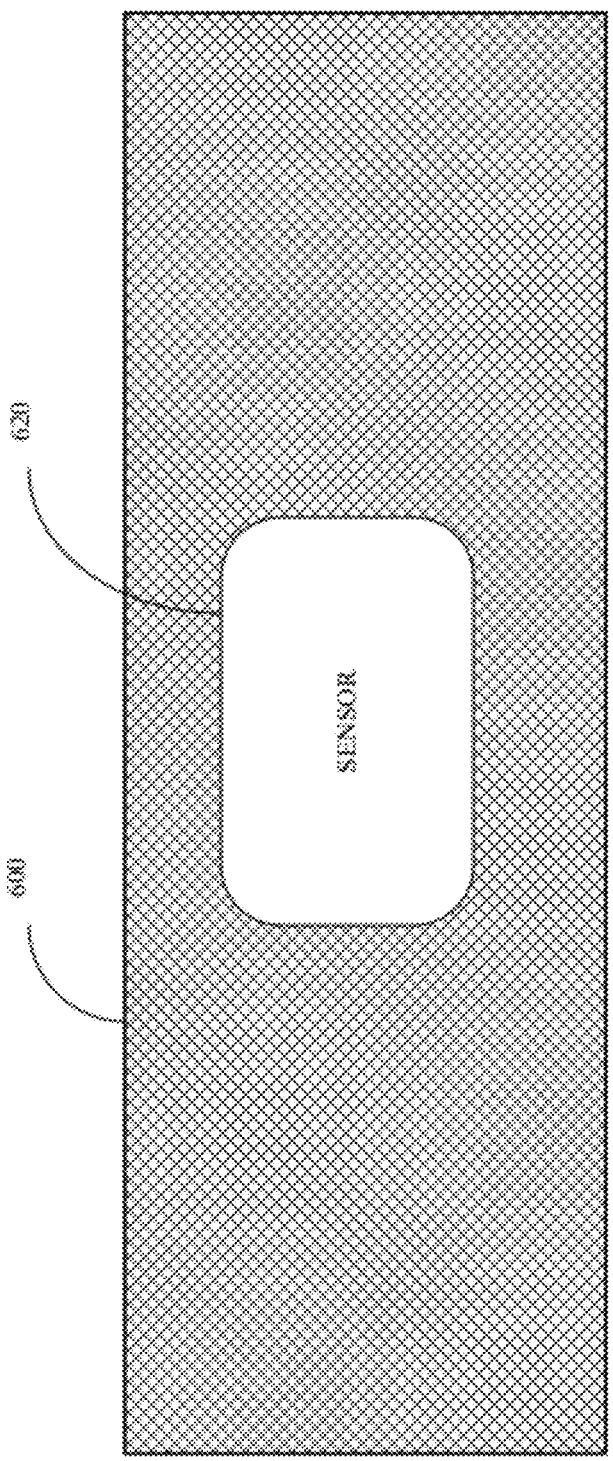
FIG. 6 is a simplified schematic illustrating a biometric sensor according to exemplary embodiments.

Referring now to FIG. 6, there is shown a sensor arrangement in accordance with an exemplary embodiment of the subject innovation. Sensors 620 can be woven into the fabric of the clothing or apparel 600. In another aspect, the sensor 620 can be incorporated into an undergarment so they are less noticeable and/or cumbersome and conform more closely to the user's body. In another aspect, some sensors, such as the gait sensor, can be embedded into the soles of shoes or other footwear.

Figure 7:
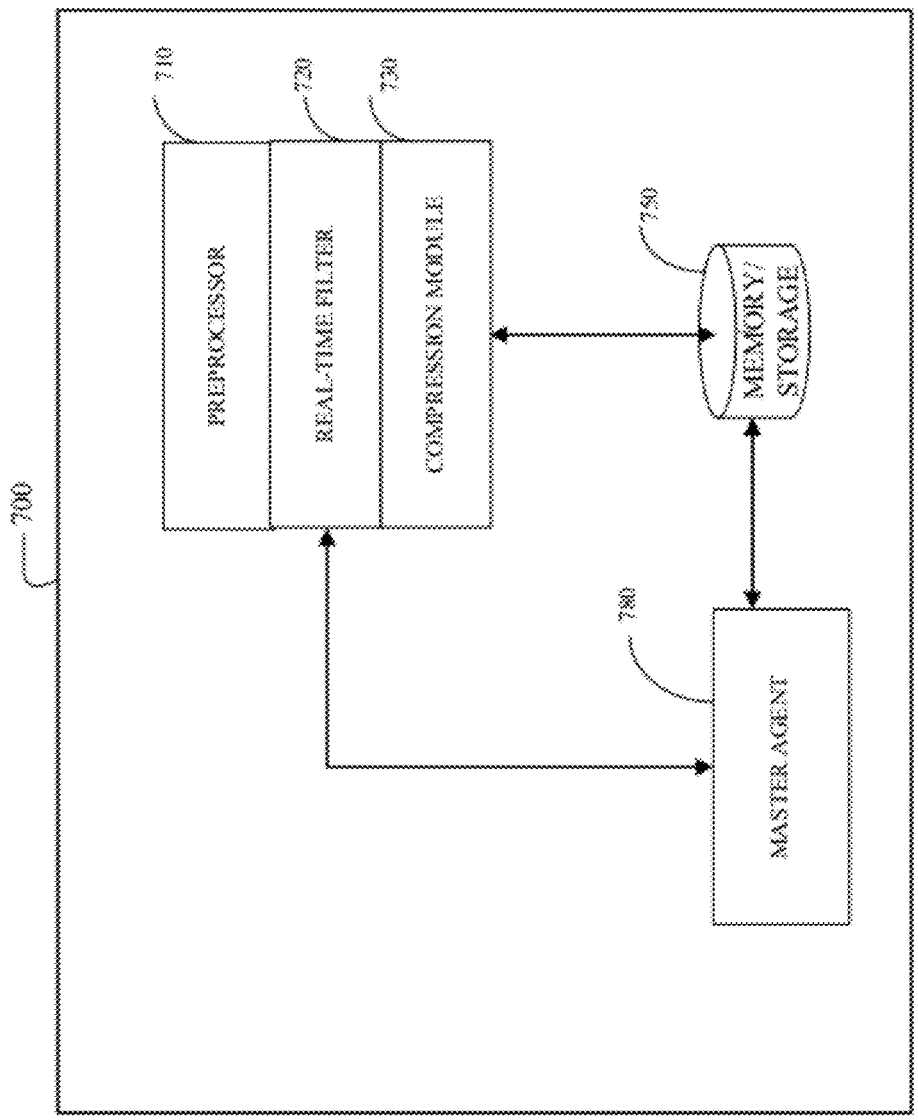
FIG. 7 is a simplified schematic illustrating a database engine according to exemplary embodiments.

Referring now to FIG. 7, there is shown a detailed schematic diagram of a database engine 700 in accordance with an exemplary embodiment of the subject innovation. The database engine 700 includes a memory/storage 750 which acts as a database. The database engine further includes a preprocessor 710, real-time filter 720, a compression module 730, and a master agent 780. The preprocessor 710 first receives the data so that various noises are removed from the data resulting in a data with a higher signal to noise ratio. In one aspect, the preprocessor 710 extracts identifiable features from the data so that windowing, sub-band transformation, mean extraction, and re-sampling may be prioritized in the extraction of data from the signal.

The real-time filter 720 then extracts or filters out data that may be necessary for archival or historical purposes from the necessary data for real-time analysis. In one aspect, the filter 720 produces a result, typically based on the entire record, based on access records which are typically not applied in athletic training. For example, if the subject is a golfer, pulse monitoring data may not be authorized or inappropriate for analysis by a golf swing coach. The real-time filter 720 applies access rules so that unauthorized data is not accessible to inappropriate personnel. In another aspect, the filter applies rule validation and administration for firewalls. Filter rules on a firewall between a secure computer network and a nonsecure computer network are validated from a user interface. A user interface is presented in which a test packet can be defined. The user interface includes controls for defining values for attributes of the test packet, wherein the attributes of the test packet are selected from a set of attributes of normal packets normally sent between the secure and nonsecure computer networks. A defined test packet is validated against a set of filter rules in the firewall or matched against the filter rules to determine those filter rules with matching attributes to the defined packet. When validating, responsive to the failure of the test packet in the validating step, the filter rule in the set of filter rules that denied the test packet is displayed. to the data is since the access rules are typically not applied within the custodian network. The results must then be filtered based on the defined rules.

The data is then transmitted to the compression module 730. The compression module 730, in one aspect, applies an efficient data compression/decompression scheme using a passive data storage media for storage of athletic performance information. The system operates on central processing hardware so that efficient storage and retrieval of information may be provided.

The memory/storage 750 acts as a database for a highly structured data storage which provides for transmission, use and security protection of the data. In one aspect, the database is a key management system wherein a plurality of keys are stored in a secure key database. A user authentication, such as a biometric authentication, is used to access the secure key database. Often the database is encrypted with a key that is accessible through user authentication.

In another aspect, the memory/storage 750 is a biometric and biomechanical data services provider (e.g., the provider of the sensors, the operator of a website, the server, the storage systems, and the database) can collect, store, and mine any of the acquired biometric data for any suitable instructional, health-related, marketing, promotional, advertising, or business objective. The biometric data can be shared among doctors, trainers, and health professionals to develop new methods to prevent or reduce injury or to help improve recovery from injury. It will be apparent that many types of devices and many wired and wireless channels of communication are possible to share biometric and biomechanical data derived from one or more sensors 120 among various users, learning centers, websites, etc. Many uses are possible and the examples discussed herein are intended to be illustrative and non-limiting.

The master agent 780 provides feedback to the athlete and acts as a "virtual" trainer or coach. In the absence of a human coach or trainer (or as a supplement thereto), the master agent analyzes the data instantaneously and provides statistical analysis and real-time feedback to the athlete. For example, the master agent collects data from multiple subjects or multiple users and processes that data to find patterns or establish norms. In some aspects, the master agent can include rules based analysis so that an individual training program is analyzed and compared to an exercise program to a previously stored reference workout or other benchmark. As a further example, the master agent can monitor an athlete workout in real time by monitoring sensor data captured and wirelessly transmitted to the trainer display system. As used herein, the term "real time" is used broadly to mean that the data is not available hours later, but is instead available within less than one hour. In a preferred aspect, the monitoring and some analysis can be done instantaneously. Advantageously, high-speed data transfer can allow monitoring to occur within a short time (e.g., less than 5 minutes) of the body movement. In some aspects, monitoring can occur within less than one minute of the body movement. In one aspect, all data is stored so that analysis of that data can be compared to other athletes and enhance the training programs automatically alerting a central network monitoring authority, with associated components is illustrated in accordance with aspects described herein.

Various other analysis of the subject's athletic performance are contemplated. For example, the master agent may apply an application for Competitive Ranking. Competitive Ranking applications such as a predominantly point goal-oriented purpose would allow access to a global ranking file archive accessed through the Internet or automatically via updated executive files. This ranking file would be created through an analysis of user participation and publishing of his/her results through Internet Web-based services.

Another example is a Downloadable Executive Program which includes graphics images would be stored in compressed or uncompressed binary forms, i.e., bitmap, gif, jpeg, etc. This new programs could be transferred to any suitable computerized position processor unit located at a remote facility via the transponder's wireless link. Therefore, the user's transponder is the node that establishes the portable network capabilities of the system, not necessarily the computerized position processor.

Custom Menu Interfaces allow a subject or a trainer or coach to customize the interface so that specialized athletic activities may require more advanced (or simplified) interfaces dependent upon the users' cognitive abilities and interactive specificity. This menu may include interactive queries or solicit information regarding the user's daily goals, subjective opinions or overall impression of the activity and ones performance which could be incorporated in the Motivation Index described below.

Various other Report Generation Tools and Templates are also contemplated. XML, HTML or other authoring language used to create documents on the Web that would provide an interactive browser-based user interface to access additional performance data analysis and report generation tools and templates that may not be available or offered with the standard product.

A Custom Performance Algorithm can include a performance analysis which is specifically tailored to the athlete and the particular sport or activity. Certain application-specific performance analysis may require dynamically linked algorithms that process and calculate non-standard or specialized information, values, units, physical measurements, statistical results, predictive behaviors, filtering, numerical analysis including differentiation and integration, convolution and correlation, linear algebraic matrices operations to compute data pose and scaling transformation, and proprietary types. One example of a proprietary type is Motivation Index, a composite numerical value derived from a weighted average of statistical performance indicators and subjective user input including relative scoring improvements, conformity to ROM pattern, lengthy activity access duration, high access rate, relative skill level improvement, daily goal achievement, etc., that could represent the overall level of enthusiasm and satisfaction, the user has for a particular activity.

As a further example, a Range of Motion (ROM) Pattern Generator provides key control points to be captured along the desired trajectory and stored in order that the algorithm can calculate an optimally smooth path, in real-time, during the comparative analysis phase. A further example is a ROM Pattern Capture & Replay so that the athlete can replay the performance. The ROM pattern can be can saved to memory in real-time by discrete position samples versus time depending upon the resolution desired and memory limitations and later played back on the transponder or remote display for analysis.

It is contemplated that other Activity Specific Attributes, including Reps/Sets, Duration, Pause, Heart Rate Limits, intra-activity delay, level, point scalars, energy expenditure, task-oriented triggers, etc., and other parametric data that controls intensity, execution rate and scoring criteria for the activity may also be measured and analyzed.

Figure 8:
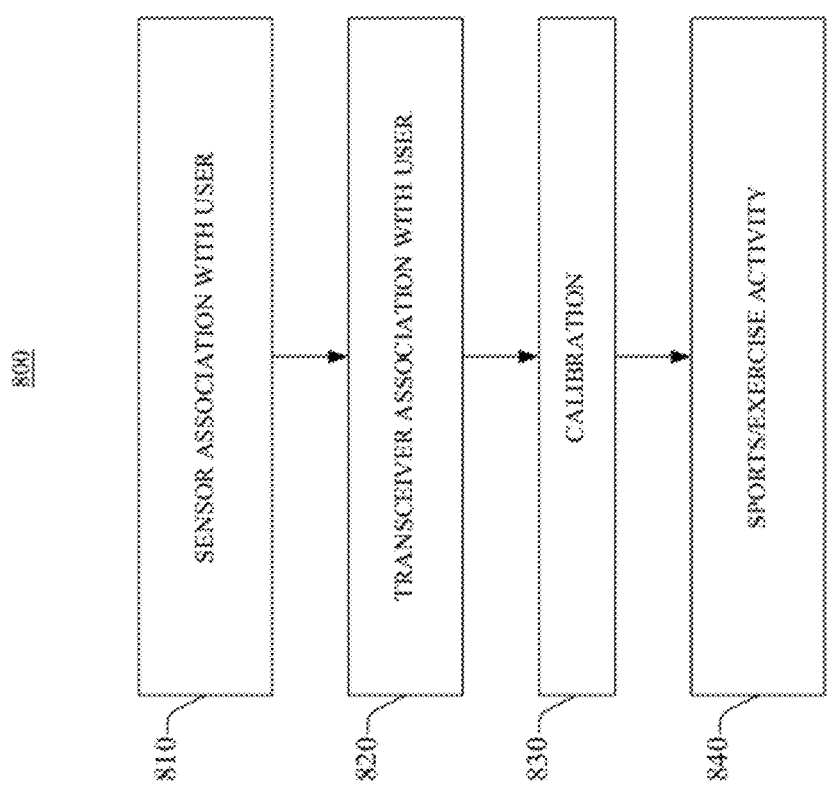
FIG. 8 is a flowchart illustrating the example steps according to exemplary embodiments.

FIG. 8 is a flowchart of an example method 800 for initializing the sensor arrangement at the commencement of a sports or athletic activity. At 810, the sensor is associated with the user. In one aspect, the step can be include the authenticating of various sensors (mating of a sensor with a transceiver) so that sensors transmit data to the appropriate transceiver. In one aspect, for a transceiver utilizing the Zigbee communication protocol, the sensors must be mated to the Zigbee controller. At 820, the transceiver is authenticated with a particular user. In one aspect, the association with a particular user includes mediating user rights at a login session, authenticate user name and password, and to manage session tokens. At 830, the sensors are calibrated for proper performance. At 840, the athlete may begin his or her sports or exercise activity.

Figure 9:
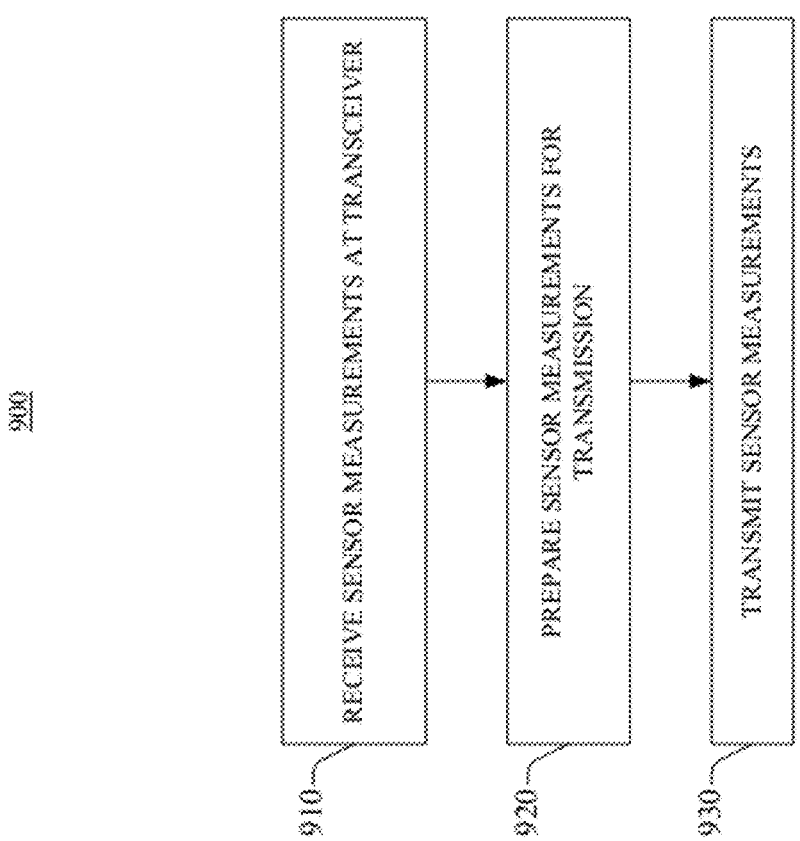
FIG. 9 is a flowchart illustrating the example steps according to exemplary embodiments.

FIG. 9 is a flowchart example of a method 900 for transceiver data transmission. At 910, the transceiver receives sensor measurements. At 920, the transceiver prepares the sensor measurements for transmission. The transceiver can collect and store data (e.g., analog and/or digital data) from the sensors. In one aspect, the data is converted from analog to digital in the sensors or the transceiver to facilitate storage and/or transmittance. In another aspect, the data is sequenced, coded, and or separated to make the reception, storage, and/or transmission more efficient. At 930, the further processed sensor data is transmitted.

FIG. 10 is a flowchart example of a method 100 for receiving and analyzing sensor data at the database engine. At 1010, the database engine receives biometric sensor data. At 1020, the preprocessor receives the sensor data so that various noises are removed from the data resulting in a data with a higher signal to noise ratio. In one aspect, the preprocessor extracts identifiable features from the data so that windowing, sub-band transformation, mean extraction, and re-sampling may be prioritized in the extraction of data from the signal.

At 1030, the real-time filter extracts or filters out data that may be necessary for archival or historical purposes from the necessary data for real-time analysis. In one aspect, the filter produces a result, typically based on the entire record, based on access records which are typically not applied in athletic training For example, if the subject is a golfer, pulse monitoring data may not be authorized or inappropriate for analysis by a golf swing coach. The real-time filter applies access rules so that unauthorized data is not accessible to inappropriate personnel. In another aspect, the filter applies rule validation and administration for firewalls. Filter rules on a firewall between a secure computer network and a nonsecure computer network are validated from a user interface. A user interface is presented in which a test packet can be defined. The user interface includes controls for defining values for attributes of the test packet, wherein the attributes of the test packet are selected from a set of attributes of normal packets normally sent between the secure and nonsecure computer networks. A defined test packet is validated against a set of filter rules in the firewall or matched against the filter rules to determine those filter rules with matching attributes to the defined packet. When validating, responsive to the failure of the test packet in the validating step, the filter rule in the set of filter rules that denied the test packet is displayed. to the data is since the access rules are typically not applied within the custodian network. The results must then be filtered based on the defined rules.

At 1040, the compression module compresses sensor data for long-term storage. The compression module, in one aspect, applies an efficient data compression/decompression scheme using a passive data storage media for storage of athletic performance information. The system operates on central processing hardware so that efficient storage and retrieval of information may be provided.

At 1050, the master agent provides feedback to the athlete and acts as a "virtual" trainer or coach. In the absence of a human coach or trainer (or as a supplement thereto), the master agent analyzes the data instantaneously and provides statistical analysis and real-time feedback to the athlete. For example, the master agent collects data from multiple subjects or multiple users and processes that data to find patterns or establish norms. In some aspects, the master agent can include rules based analysis so that an individual training program is analyzed and compared to an exercise program to a previously stored reference workout or other benchmark. As a further example, the master agent can monitor an athlete workout in real time by monitoring sensor data captured and wirelessly transmitted to the trainer display system. As used herein, the term "real time" is used broadly to mean that the data is not available hours later, but is instead available within less than one hour. In a preferred aspect, the monitoring and some analysis can be done instantaneously. Advantageously, high-speed data transfer can allow monitoring to occur within a short time (e.g., less than 5 minutes) of the body movement. In some aspects, monitoring can occur within less than one minute of the body movement. In one aspect, all data is stored so that analysis of that data can be compared to other athletes and enhance the training programs automatically alerting a central network monitoring authority, with associated components is illustrated in accordance with aspects described herein.

As employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "store," "data store," "data storage," "database," "repository," and substantially any other information storage component relevant to operation and functionality of a component, refer to "memory components," or entities embodied in a "memory" or components comprising the memory. It will be appreciated that the memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Various aspects or features described herein may be implemented as a method, apparatus, or article of manufacture using standard programming and/or engineering techniques. In addition, various aspects disclosed in the subject specification can also be implemented through program modules stored in a memory and executed by a processor, or other combination of hardware and software, or hardware and firmware. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disc (CD), digital versatile disc (DVD), blu-ray disc (BD) . . . ), smart cards, and flash memory devices (e.g., card, stick, key drive . . . ).

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components can be combined into a single component providing aggregate functionality or divided into several separate sub-components, and that any one or more middle layers, such as a management layer, can be provided to communicatively couple to such sub-components in order to provide integrated functionality. Any components described herein may also interact with one or more other components not specifically described herein but generally known by those of skill in the art.

In view of the exemplary systems described supra, methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, can be implemented which achieve the same or a similar result. Moreover, not all illustrated blocks are required to implement the methodologies described hereinafter.

It should be appreciated that while various aspects, features, or advantages described herein have been illustrated through femto access point(s) and associated femto coverage, such aspects and features also can be exploited for home access point(s) (HAPs) that provide wireless coverage through substantially any, or any, disparate telecommunication technologies, such as for example Wi-Fi (wireless fidelity) or picocell telecommunication. Additionally, aspects, features, or advantages of the subject innovation can be exploited in substantially any wireless telecommunication, or radio, technology; for example, Wi-Fi, Worldwide Interoperability for Microwave Access (WiMAX), Enhanced General Packet Radio Service (Enhanced GPRS), 3GPP LTE, 3GPP2 UMB, 3GPP UMTS, HSPA, HSDPA, HSUPA, or LTE Advanced. Moreover, substantially all aspects of the subject innovation can include legacy telecommunication technologies.

What has been described above includes examples of the various embodiments. It is, of course, not possible to describe every conceivable combination of components or methodologies for purposes of describing the various embodiments, but one of ordinary skill in the art may recognize that many further combinations and permutations of the subject embodiments are possible. Accordingly, the various embodiments are intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects. In this regard, it will also be recognized that the various embodiments include a system as well as a computer-readable medium having computer-executable instructions for performing the acts and/or events of the various methods.

In addition, while a particular feature may have been disclosed with respect to only one of several implementations, such feature may be combined with one or more other features of the other implementations as may be desired and advantageous for any given or particular application. Furthermore, to the extent that the terms "includes," and "including" and variants thereof are used in either the detailed description or the claims, these terms are intended to be inclusive in a manner similar to the term "comprising."

What is claimed is:

1. A system, comprising:
   a memory to store instructions; and
   a processor, coupled to the memory, to facilitate execution of the instructions to perform operations, comprising:
      receiving biometric data related to a subject determined to be performing a defined sports activity and associated with movements of a body of the subject gathered by a sensor from a wireless transceiver coupled to the sensor; and determining feedback associated with the biometric data,
wherein the feedback comprises an instruction associated with the defined sports activity based on the biometric data.

2. The system of claim 1, wherein the real-time feedback is provided based on a rules-based analysis of the biometric data.

3. The system of claim 1, wherein the real-time feedback is provided based on a comparison to other biometric data from a second subject.

4. The system of claim 1, wherein the biometric data is utilized for a competitive analysis between the subject and a third subject performing the sports activity.

5. The system of claim 1, wherein the determining the feedback further comprises:
comparing the biometric data to previous biometric data stored in a database,
wherein the feedback is based on the comparison.

6. The system of claim 5, wherein the
feedback is statistical feedback based on the comparison.

7. The system of claim 1, wherein the comparison is based on a benchmark derived from previously stored biometric data related to the sports activity.

8. The system of claim 7, wherein the benchmark is derived from biometric data related to other subjects engaging in the sports activity.

9. The system of claim 1, wherein the wireless transceiver comprises:
a Zigbee communication module to facilitate communication with the sensor via the Zigbee communication protocol.

10. The system of claim 1, wherein the feedback is provided to the wireless transceiver via the Wi-Fi protocol.

11. The system of claim 1, wherein the wireless transceiver facilitates presenting the feedback to the subject through an interactive voice response (IVR) interface.

12. The system of claim 1, wherein the instruction comprises an audio instruction from a coach.

13. The system of claim 12, wherein the audio instruction is selected from a set of instructions from the coach stored in a database.

14. The system of claim 1, wherein the defined sports activity comprises a rehabilitation activity.

15. A method, comprising:
receiving, by a system comprising a processor, biometric data related to a body movement of a performance of a subject gathered by a sensor from a wireless transceiver coupled to the sensor; and
generating, by the system, feedback associated with the biometric data, wherein the feedback comprises statistical feedback based on a rules-based analysis related to a parameter associated with a defined sports activity and an instruction based on the statistical feedback.

16. The method of claim 15, wherein the parameter is related to second biometric data associated with a second subject.

17. The method of claim 15, further comprising compressing the biometric data for storage.

18. The method of claim 15, wherein the generating the feedback comprises comparing the biometric data to benchmark data from a previously stored sports activity.

19. The method of claim 15, wherein the generating the feedback further comprises replaying a previously stored sports activity.

20. The method of claim 15, wherein the generating the feedback comprises comparing the biometric data to benchmark data from another subject other subjects.

21. The method of claim 15, further comprising receiving, by the system, the biometric data at a Zigbee communication module.

22. The method of claim 15, further comprising receiving, by the system, the biometric data according to a Zigbee communication protocol.

23. The method of claim 15, further comprising receiving, by the system, the biometric data according to a Wi-Fi protocol.

24. The method of claim 15, further comprising presenting, by the system, the coaching instruction to the subject through an interactive voice response (IVR) interface.

25. The method of claim 15, wherein the rules-based analysis comprises collecting data from multiple users associated with the defined sports activity and creating a benchmark.

26. The method of claim 15, wherein the biometric data is available within one hour or less from the defined sports activity.

27. The method of claim 15, wherein the biometric data is available within five minutes or less from the defined sports activity.

28. An apparatus, comprising:
a memory for storing instructions; and
a processor, coupled to the memory, to facilitate execution of the instructions to perform operations, comprising:
receiving biometric data related to a subject associated with movements of a body of the subject engaged in a defined athletic activity gathered by a sensor from a wireless transceiver coupled to the sensor; and
determining feedback associated with the biometric data to facilitate monitoring the subject,
wherein the feedback comprises an instruction associated with the defined athletic activity determined based on the biometric data, and
wherein the instruction associated with the defined sports activity is displayed in an auditory form in response to the receiving of the biometric data.

29. The system of claim 28, wherein the feedback is determined by a rules-based analysis based on the biometric data.

30. The system of claim 28, wherein the feedback is determined based on biometric data related to a second subject.

31. The system of claim 28, wherein the feedback is utilized for a competitive analysis.

32. The system of claim 28, wherein the operations further comprise:
compressing the biometric data to facilitate storage.

33. The system of claim 28, wherein the wireless transceiver comprises:
a Zigbee communication module.

34. The system of claim 28, wherein the feedback is provided to the wireless transceiver via a Zigbee communication protocol.

35. The apparatus of claim 28, wherein the instruction comprises an advertisement based on the biometric data.

36. The apparatus of claim 28, wherein the operations further comprise providing the biometric data and the feedback to a doctor identity associated with the subject.

* * * * *